US005939400A

United States Patent [19]
Steinman et al.

[11] Patent Number: 5,939,400
[45] Date of Patent: *Aug. 17, 1999

[54] DNA VACCINATION FOR INDUCTION OF SUPPRESSIVE T CELL RESPONSE

[75] Inventors: Lawrence Steinman, Palo Alto, Calif.; Ari Waisman, Tel-Aviv, Israel

[73] Assignee: The Board of Trustees of The Leland Stanford Junior University, Palo Alto, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/606,639

[22] Filed: Feb. 26, 1996

[51] Int. Cl.$^6$ .......................... A01N 43/04; A61K 31/70; C12N 15/00; C12N 15/63
[52] U.S. Cl. ........................ 514/44; 435/455; 435/320.1; 435/69.1; 800/9; 424/9.21
[58] Field of Search .......................... 514/44; 435/320.1, 435/69.1, 240.2, 172.3, 455; 424/9.2, 9.21; 800/9

[56] References Cited

PUBLICATIONS

Waisman et al., Nature Medicine, vol. 2, pp. 899–905, Aug. 1996.
Orkin et al., Report and Recommendation of the Panel to Assess the NIH Investment in Research on Gene Therapy, Dec. 7, 1995.
Coghlan, Focus, vol. 148, pp. 14–15, Nov. 25, 1995.
Brown, "News Media, Researchers 'Oversold' Gene Therapy, Advisory Panel Says", The Washington Post, Dec. 8, 1995.
Marshall, Science, vol. 269, pp. 1050–1055, Aug. 25, 1995.
Anderson, Human Gene Therapy, vol. 5, pp. 281–282, 1994.
Challita & Kohn, Procedures of the National Academy of Sciences, U.S.A., vol. 91, pp. 2567–2571, Mar. 1994.
Jaroff, Time, vol. 148, pp. 24–29, Sep. 1996.
Vandenbark et al., Nature, vol. 341, pp. 541–544, 1989.
Steinman, Cell, vol. 80, pp. 7–10, Jan. 13, 1995.
Chou et al., Procedures of the National Academy of Sciences, U.S.A., vol. 84, pp. 1992–1996, 1987.
Steinman, L., (1996), "A few autoreactive cells in an autoimmune infiltrate control a vast population of nonspecific cells: A tale of smart bombs and the infantry," Proc. Natl. Acad. Sci. USA, 93, 2253–56.
Xu and Liew, "Protection Against Leishmaniasis by Injection of DNA Encoding a Major Surface Glycoprotein, gp63, of L. major," Immunology (1995), 84:173–176.
Mor et al., "Complexity of the Cytokine and Antibody Response Elicited by Immunizing Mice with Plasmodium Yoelii Circumsporozoite Protein Plasmid DNA," J. of Immunology (1995), 2039–2046.
Katz et al., "T Helper Cell Subsets in Insulin–Dependent Diabetes," Science (May 1995), 268:1185–1188.
Rohane et al., "Islet–Infiltrating Lymphocytes from Prediabetic NOD Mice Rapidly Transfer Diabetes to NOD–scid/scid Mice," Diabetes (May 1995), 44:550–554.
Weiner et al., "Oral Tolerance: Immunologic Mechanisms and Treatment of Animal and Human Organ–Specific Autoimmune Diseases by Oral Administration of Autoantigens," Annu. Rev. Immunol. (1994), 12:809–837.
Davis et al., "Direct Gene Transfer in Skeletal Muscle: Plasmid DNA–based Immunization Against the Hepatitis B Virus Surface Antigen," Vaccine (1994), 12:1503–1509.
Davis et al., "DNA–Based Immunization Induces Continuous Secretion of Hepatitis B Surface Antigen and High Levels of Circulating Antibody," Human Molecular Genetics (1993), 2:1847–1851.
Ulmer et al., Heterologous Protection Against Influenza by Injecting of DNA Encoding a Viral Protein, Science (Mar. 1993), 259:1745–1749.
Martin et al., "Diversity in Fine Specificity and T Cell Receptor Usage of The Human CD4$^+$ Cytotoxic T Cell Response Specific For the Immunodominant Myelin Basic Protein Peptide 87–106," J. of Immunology (Mar. 1992), 148:1359–1366.
Tang et al., "Genetic Immunization is a Simple Method for Eliciting an Immune Response," Nature (Mar. 1992), 356:152–154.
Martin et al., "A Myelin Basic Protein Peptide is Recognized by Cytotoxic T Cells in the Context of Four HLA–DR Types Associated with Multiple Sclerosis," J. of Experimental Medicine (Jan. 1991), 173:19–24.
Wraith et al., "Antigen Recognition in Autoimmune Encephalomyelitis and the Potential for Peptide–Mediated Immunotherapy," Cell (Oct. 1989), 59:247–255.
Wraith et al., "T Cell Recognition as the Target For Immune Intervention in Autoimmune Disease," Cell (Jun. 1989), 57:709–715.
Acha–Orbea et al., "Limited Heterogeneity of T Cell Receptors from lymphocytes Mediating Autoimmune Encephalomyelitis Allows Specific Immune Intervention," Cell (Jul. 1988), 54:263–273.

*Primary Examiner*—Deborah Crouch
*Assistant Examiner*—Jill D. Martin
*Attorney, Agent, or Firm*—Bozicevic, Field & Francis LLP; Pamela J. Sherwood

[57] ABSTRACT

A pro-inflammatory T response is specifically prevented by the injection into a recipient of DNA encoding the variable region of a T cell receptor. In response to the vaccination, T cells expressing the variable region produce Th2 cytokines, including IL-4. A pro-inflammatory T cell response directed to an autoantigen is shown to be suppressed by DNA vaccination. The suppressive vaccination further reduced the inflammatory effect of T cells reactive against epitopes of the autoantigen not recognized by the variable region used for vaccination.

6 Claims, 5 Drawing Sheets

FIGURE 2A pAc1-20 Concentration (µg/ml)

DNA VACCINATION FOR INDUCTION OF SUPPRESSIVE T CELL RESPONSE

This invention was made with government support from the National Institutes of Health. The Government may have certain rights in this invention.

INTRODUCTION

1. Background

The complexity of the immune system has been a daunting barrier to an understanding of immune system dysfunction. In recent years, the techniques of molecular biology have provided insight into the mechanisms and components that underlie immunity. To a large extent, the story of immunity is the story of lymphocytes. Lymphocytes possess an extremely complex and subtle system for interacting with each other, with antigen-presenting cells, and with foreign antigens and cells.

Modulation of the immune response varies with the specific factors produced, and the receptors present on the responding cell. The pathways for down-regulating responses are as important as those required for activation. T cell tolerance is one well-known mechanism for preventing an immune response to a particular antigen. Other mechanisms, such as secretion of suppressive cytokines, are also known.

A common feature in a number of diseases and inflammatory conditions is the involvement of pro-inflammatory $CD4^+$ T cells. These T cells are responsible for the release of inflammatory, Th-1 type cytokines. Cytokines characterized as Th-1 type include interleukin 2 (IL-2), $\gamma$-interferon, TNF$\alpha$ and IL-12. Such pro-inflammatory cytokines act to stimulate the immune response, in many cases resulting in the destruction of autologous tissue. Other cytokines are associated with suppression of T cell response. These are the Th2 type, and include IL-10, IL-4 and TGF-$\beta$. It has been found that Th1 and Th2 type T cells may use the identical antigen receptor in response to an immunogen; in the former producing a stimulatory response and in the latter a suppressive response.

Many clinical symptoms associated with inflammatory diseases could be reduced by induction of a specific suppressive response. Immunosuppressive drugs, such as cyclosporin A, have been used in therapy. Their lack of specificity, however, is a severe drawback. Treatment that specifically inhibits T cell activation would be of great medical benefit.

2. Relevant Literature

The injection of DNA to promote vaccination against microbes and tumors is discussed in Pardoll et al. (1995) *Immunity* 3:165–169; Davis et al. (1993) *Hum. Mol. Genet.* 2:1847–1851; Ulmer et al. (1993) *Science* 259:1745–1749; and Tang et al. (1992) *Nature* 356:152–154. Genetic immunization has demonstrated induction of both a specific humoral but also a more broadly reacting cellular immune response in animal models of cancer, mycoplasma, TB, malaria, and many virus infections, including influenza and HIV. See, for example, Mor et al. (1995) *J Immunol* 155:2039–46; Xu and Liew (1995) *Immunology* 84:173–6; and Davis et al. (1994) *Vaccine* 12:1503–9.

In EAE it has been shown that Th2 type cells prevent induction of disease, Weiner et al. (1994) *Annu. Rev. Immunol.* 12:809–837. It has been shown that Th1 type cells induce severe arthritis in a mouse model, Germann et al. (1995) *P.N.A.S.* 92:4823–4827. Sempe et al. (1994) *Diabetologia* 37:337–343 provides evidence of CD4+ regulatory T cells in the NOD male mouse. T cell mediated inhibition of the transfer of autoimmune diabetes in NOD mice is demonstrated in Hutchings and Cooke (1990) *J. Autoimmun.* 3:175–185.

The administration of monoclonal antibodies directed to pathogenic TCR V gene products, and vaccination with peptides from the second and third complementarity determining region of the pathogenic TCR V region have proven successful in the therapy of EAE, shown in Acha-Orbea et al. (1988) *Cell* 54:263–273; Sakai et al. (1988) *P.N.A.S.* 85:8608–8612; Vandenbark et al. (1989) *Nature* 341:541–544; and Howell et al. (1989) *Science* 246:668–670.

Susceptibility to MS has been associated with certain MHC Class II genes, Oksenberg and Steinman (1990) *Current Opinion in Immunology* 2:619–621. At the cellular level, oligoclonality of T-cells has been described in the cerebrospinal fluid (CSF) of MS patients, Lee et al., *Ann. Neurol.* 29:33–40 (1991). Oksenberg et al., *Nature* 345:344–346 (1990) describes the use of PCR to amplify TCR V$\alpha$ sequences from transcripts derived from MS brain lesions. Wucherpfennig et al. *Science* 248:1016–1019 (1990) and Ota et al., *Nature* 346:183 (1990) report studies of T-cell clones in man that recognize myelin basic protein.

SUMMARY OF THE INVENTION

Methods are provided for the induction of a specific, suppressive T cell response. A mammalian host is vaccinated with a DNA expression vector encoding a soluble T cell receptor variable region antigen ($V_{Vaccine}$). In response to the vaccination, a suppressive response is evoked, where T cells expressing the variable region (targeted variable region, "$V_{Target}$") produce Th2 cytokines, including IL4. Suppressive vaccination prevents or reverses T cell pro-inflammatory responses in a specific, targeted manner. Conditions that benefit from this treatment include autoimmune diseases, tissue transplantation and other diseases associated with inflammation.

BRIEF DESCRIPTION OF THE DRAWINGS

FIGS. 2A to 2D are graphs showing the alteration of cytokine production by DNA vaccination. The proliferative response is shown in FIG. 2A for draining lymph node cells from PL/J mice immunized with MBP Ac1-20 after pre-treatment with DNA coding for V$\beta$5.1 (□), V$\beta$8.2 (○), or with PBS only (■). Supernatants of LNC from mice pre-treated with V$\beta$5.1 (■), V$\beta$8.2 (■), or with PBS only (▨) were activated with Concanavalin A (10 $\mu$g/ml) or the peptide MBP Ac1-20 were tested for the presence of $\gamma$-interferon (FIG. 2B), IL-2 (FIG. 2C) and IL-4 (FIG. 2D).

FIGS. 3A and 3B show disease induction by T cell lines. T cell lines isolated from control PL/j with EAE (■) or from mice protected with the V$\beta$8.2 DNA, 8.2-LN (●) were inoculated into female PL/J mice intravenously, 5 million cells/mouse. The mean disease score of all the mice in each group is shown, ±SD. In FIG. 3B, five million TH2 cells directed to MBP Ac1-20 derived from mice immunized with Vβ8.2 DNA were able to suppress EAE (●), whereas mice receiving MBP Ac1-20 in CFA develop EAE (■).

DESCRIPTION OF THE SPECIFIC EMBODIMENTS

The subject methods provide a means for therapeutic treatment and investigation of inflammation, through the induction of a specific, suppressive T-cell response. A DNA expression cassette is injected into host tissue, for example muscle or skin. The vector comprises a DNA sequence encoding at least a portion of the variable region from a T cell antigen receptor associated with a phenotype of interest ($V_{Vaccine}$). In response to this vaccination, a suppressive response is evoked. Endogenous T cells expressing a native form of the targeted variable region, "$V_{Target}$" produce suppressive, Th2 cytokines, including IL-4.

Suppressive vaccination finds use in the treatment of autoimmune diseases characterized by the involvement of pro-inflammatory T cells, such as multiple sclerosis, experimental autoimmune encephalitis, rheumatoid arthritis and insulin dependent diabetes mellitus. Other conditions that may be treated include graft v. host disease, graft rejection, inflammation of the central nervous system caused by bacterial and viral infection, e.g. inflammatory response to vaccination with live microorganisms, local inflammation in response to trauma, and other conditions associated with undesirable, e.g. pathogenic T cell activity. Animal models, particularly small mammals, e.g. murine, lagomorpha, etc. are of interest for experimental investigations.

A common feature in a number of diseases and inflammatory conditions is the involvement of pro-inflammatory $CD4^+$ T cells. These T cells are responsible for the release of inflammatory, Th-1 type cytokines at the site of tissue destruction. Such pro-inflammatory cytokines act to stimulate the immune response, in many cases resulting in the destruction of autologous tissue. Suppressive vaccination serves both to induce specific suppression from T cells expressing the specific variable region, and to release suppressive cytokines at the site of inflammation, thereby counteracting the effect of Th-1 type cytokines. The variable region(s) for vaccination will be chosen to optimize these effects.

A DNA expression cassette encoding at least a portion of a T cell receptor variable region, usually as part of a vector, is introduced into tissue of the vaccine recipient. The variable region gene or portion thereof ($V_{vaccine}$) is expressed in the tissue, and the encoded polypeptide acts as an immunogen, or antigen. It may be hypothesized that the presentation of the $V_{vaccine}$ sequence by a "non-professional" cell, lacking co-stimulatory molecules such as CD80 and CD86, stimulates a suppressive T cell response.

The $V_{vaccine}$ sequence encodes at least a portion of the variable region of a T cell antigen receptor, e.g. $TCR_\beta$, $TCR_\alpha$, $TCR_\gamma$, and $TCR_\delta$. By "variable region" is intended any of the gene segments V, D and/or J, in germline or rearranged form. Of particular interest are the V segments from the $TCR_\alpha$ and $TCR_\beta$ locus. The sequences of T cell antigen receptor variable regions have been described in detail, and are well-known in the art. These variable regions are characterized by genetic rearrangement during the maturation of T lymphocytes, such that the chromosomal V segment is joined to a "D" and/or a "J" segment, thereby allowing expression of a complete α or β chain. A complex of the αβ or γδ heterodimer and accessory molecules recognizes antigenic peptides bound to MHC class I or class II molecules.

The $V_{vaccine}$ sequence may be from any mammalian or avian species, e.g. primate spa, particularly humans; rodents, including mice, rats and hamsters; rabbits; equines, bovines, canines, felines; etc. Of particular interest are the human and mouse TCR V segments. Generally, the $V_{vaccine}$ sequence will have the same species of origin as the animal host, preferably it will be autologous. Exemplary sequences may be found in Kabat et al. *Sequences of Proteins of Immunological Interest,* NIH Publication No. 91-3242, pp 1477–1571, or accessed from the Genbank database. Among Vα families of interest are human Vα8-10, Vα12 and Vα16. Other regions of interest include Vα1, Vα5 and Vα7. Vβ families of interest include human Vβ5, Vβ6, Vβ7 and Vβ12, particularly Vβ5.1 and Vβ5.2. Exemplary V regions are the mouse Vβ8.2 and $V_\beta17a$ sequences, and their respective human counterparts, the $V_\beta12$ and $V_\beta4$ subfamilies. Methods for selection of $V_{vaccine}$ sequences in relation to a particular disease are provided.

The subject DNA expression cassette will comprise most or all of the sequence encoding a TCR variable region, as defined by Kabat et al., supra. The coding sequence may be truncated at the 5' or 3' terminus, usually at least about 75% of the V segment sequence will be present, more usually at least about 80%, and preferably at least about 95%. The sequence will be sufficient to induce a suppressive response by $V_{target}$ cells on vaccination. Optionally, the $V_{vaccine}$ will include DNA sequences coding for the T cell receptor D, J or DJ segments, where the D or J segment will be contiguous with the V region sequence at the 3' end.

The vaccine may be formulated with one or a cocktail of $V_{vaccine}$ sequences. While it has been found that a single sequence is capable of suppressing a response to multiple epitopes, it may be desirable in some cases to include multiple $V_{vaccine}$ sequences, where each recognizes a different epitope, or epitope-MHC combination.

The $V_{Vaccine}$ sequences are inserted into an appropriate expression cassette. The expression construct is prepared in conventional ways. The cassette will have the appropriate transcriptional and translational regulatory sequences for expression of the $V_{Vaccine}$ sequence in the vaccine recipient cells. The cassette will generally be a part of a vector, which contains a suitable origin of replication, and such genes encoding selectable markers as may be required for growth, amplification and manipulation of the vector, prior to its introduction into the recipient. Suitable vectors include plasmids, YACs, BACs, bacteriophage, retrovirus, and the like. Conveniently, the expression vector will be a plasmid. Prior to vaccination, the cassette may be isolated from vector sequences by cleavage, amplification, etc. as known in the art. For injection, the DNA may be supercoiled or linear, preferably supercoiled. The cassette may be maintained in the host cell for extended periods of time, or may be transient, generally transient. Stable maintenance is achieved by the inclusion of sequences that provide for integration and/or maintenance, e.g. retroviral vectors, EBV vectors and the like.

The expression cassette will generally employ an exogenous transcriptional initiation region, i.e. a promoter other than the promoter which is associated with the T cell receptor in the normally occurring chromosome. The promoter is functional in host cells, particularly host cells targeted by the cassette. The promoter may be introduced by recombinant methods in vitro, or as the result of homologous integration of the sequence by a suitable host cell. The promoter is operably linked to the coding sequence of the $V_{vaccine}$ to produce a translatable mRNA transcript. Expression vectors conveniently will have restriction sites located near the promoter sequence to facilitate the insertion of $V_{vaccine}$ sequences.

Expression cassettes are prepared comprising a transcription initiation region, which may be constitutive or inducible, the gene encoding the $V_{Vaccine}$ sequence, and a transcriptional termination region. The expression cassettes may be introduced into a variety of vectors. Promoters of interest may be inducible or constitutive, usually constitutive, and will provide for high levels of transcription in the vaccine recipient cells. The promoter may be active only in the recipient cell type, or may be broadly active in many different cell types. Many strong promoters for mammalian cells are known in the art, including the β-actin promoter, SV40 early and late promoters, immunoglobulin promoter, human cytomegalovirus promoter, retroviral LTRs, etc. The promoters may or may not be associated with enhancers, where the enhancers may be naturally associated with the particular promoter or associated with a different promoter.

A termination region is provided 3' to the coding region, where the termination region may be naturally associated with the variable region domain or may be derived from a different source. A wide variety of termination regions may be employed without adversely affecting expression.

The various manipulations may be carried out in vitro or may be performed in an appropriate host, e.g. *E. coli*. After each manipulation, the resulting construct may be cloned, the vector isolated, and the DNA screened or sequenced to ensure the correctness of the construct. The sequence may be screened by restriction analysis, sequencing, or the like.

A small number of nucleotides may be inserted at the terminus of the $V_{vaccine}$ sequence, usually not more than 20, more usually not more than 15. The deletion or insertion of nucleotides will usually be as a result of the needs of the construction, providing for convenient restriction sites, addition of processing signals, ease of manipulation, improvement in levels of expression, or the like. In addition, one may wish to substitute one or more amino acids with a different amino acid for similar reasons, usually not substituting more than about five amino acids in the region.

The vaccine may be formulated with one or a cocktail of $V_{vaccine}$ sequences, which may be on the same or different vectors. The DNA vectors are suspended in a physiologically acceptable buffer, generally an aqueous solution e.g. normal saline, phosphate buffered saline, water, etc. Stabilizing agents, wetting and emulsifying agents, salts for varying the osmotic pressure or buffers for securing an adequate pH value, and skin penetration enhancers can be used as auxiliary agents. The DNA will usually be present at a concentration of at least about 1 ng/ml and not more than about 10 mg/ml, usually at about from 100 $\mu$g to 1 mg/ml. The vaccine may be fractionated into two or more doses, of at least about 1 $\mu$g, more usually at least about 100 $\mu$g, and preferably at least about 1 mg per dose, administered from about 4 days to one week apart.

The DNA vaccine is injected into muscle or other tissue subcutaneously, intradermally, intravenously, orally or directly into the spinal fluid. Of particular interest is injection into skeletal muscle. An example of intramuscular injection may be found in Wolff et al. (1990) *Science* 247:1465–1468. Jet injection may also be used for intramuscular administration, as described by Furth et al. (1992) *Anal Biochem* 205:365–368. The DNA may be coated onto gold microparticles, and delivered intradermally by a particle bombardment device, or "gene gun". Microparticle DNA vaccination has been described in the literature (see, for example, Tang et al. (1992) *Nature* 356:152–154). Gold microprojectiles are coated with the vaccine cassette, then bombarded into skin cells.

The efficiency of DNA vaccination may be improved by injection of cardiotoxin into the tissue about one week prior to the vaccination, as described by Davis et al. (1993) *FEBS Lett.* 333:146–150, and in the examples. The cardiotoxin stimulates muscle degeneration and regeneration. The muscle is injected with from about 0.1 to 10 $\mu$M of cardiotoxin dissolved in a pharmacologically acceptable vehicle.

The condition that is being treated will determine the choice of $V_{vaccine}$ sequence(s). Identification of specific T-cell receptor variable regions associated with inflammatory disease allows therapies to be employed that inhibit the pro-inflammatory response of T-cells having such variable regions ($V_{target}$). Variable regions associated with disease are identified by a number of different methods. In the case of autoimmune diseases, T cells have been identified that specifically react with a combination of an autoantigen presented by autologous MHC molecules.

For example, in vitro studies may be performed to identify the variable region configuration of T cells that respond to a test antigen, e.g. autoantigen, graft histocompatibility antigen, viral antigen, etc. The assay may utilize whole antigen, or select immunodominant peptides, using methods known in the art to select and prepare peptides. The responding T cells may be autologous, syngeneic or allogeneic with respect to the vaccine recipient. The responding cells are selected, and the expressed T cell receptor genes identified, for example by polymerase chain reaction amplification using primers that hybridize with conserved sequences. The variable region of the responding T cell receptor may then be used for vaccination to suppress T cell reactivity in vivo against the test antigen.

Alternatively, $V_{Target}$ expression alone or in conjunction with the $J_{Target}$ may be determined for T-cells found at the site of inflammatory lesions. For example, the T cells from the site of inflammation are isolated, and total mRNA is prepared according to standard procedures. RT-PCR, or other amplification methods known in the art, is used to amplify the expressed variable region. In the case RT-PCR, primers are employed that will identify the particular variable region that is expressed. Primers are selected in accordance with the known sequences of conserved regions of the T-cell receptor subunits. The particular V regions and J regions expressed by T-cells present in the lesion are then related to the host MHC antigen type.

Genomic DNA may be isolated from such T cells, and used to determine the presence of rearrangements at the TCR locus, by having primers that hybridize to substantially conserved regions of the variable region. By cloning, the locus can be sequenced, and the variable region identity established.

A 100% correlation between the expression of a variable region and the presence of the disease in question is normally not to be expected, nor will it be necessarily achieved. It will usually be satisfactory that in at least 60%, preferably 70%, of the hosts positive for the disease, the variable region locus associated with the disease is expressed in a population of host T-cells. Similarly, in fewer than about 50%, preferably in fewer than about 30% of the hosts which do not present the symptoms of the disease, the variable region is absent.

T-cells with a shared variable region will express the variable region gene from a single V segment subfamily.

Gene segments that display greater than 75% nucleotide sequence similarity over the length of the V gene are considered members of the same subfamily (Crew et al. (1981) Cell 25:59–66). The sequence similarity is calculated for the V exon itself, and does not include sequences encoded by the D and J segments and N additions.

Depending upon the particular disease, various tissues may be employed for identifying the T-cells. For neural diseases such as multiple sclerosis, brain plaques or cerebrospinal fluid may be employed as a source of the T-cells. Similarly, for myasthenia gravis, muscle, thymus tissue or T-cells responsive to acetylcholine receptor may be employed. For rheumatoid arthritis, the synovium may be employed.

By identifying a particular Class II haplotype or molecular phenotype, one can then identify particular Vα and Vβ variable regions associated with a particular disease. Once the disease associated T-cell receptor or variable regions are identified, one may than use suppressive vaccination for prophylaxis or treatment.

The subject therapy will desirably be administered during the presymptomatic or preclinical stage of the disease, and in some cases during the symptomatic stage of the disease. Early treatment is preferable, in order to prevent the loss of function associated with inflammatory tissue damage. The presymptomatic, or preclinical stage will be defined as that period not later than when there is T cell involvement at the site of disease, e.g. islets of Langerhans, synovial tissue, thyroid gland, etc., but the loss of function is not yet severe enough to produce the clinical symptoms indicative of overt disease. T cell involvement may be evidenced by the presence of elevated numbers of T cells at the site of disease, the presence of T cells specific for autoantigens, the release of performs and granzymes at the site of disease, response to immunosuppressive therapy, etc.

Degenerative joint diseases may be inflammatory, as with seronegative spondylarthropathies, e.g. ankylosing spondylitis and reactive arthritis; rheumatoid arthritis; gout; and systemic lupus erythematosus. The degenerative joint diseases have a common feature, in that the cartilage of the joint is eroded, eventually exposing the bone surface. Destruction of cartilage begins with the degradation of proteoglycan, mediated by enzymes such as stromelysin and collagenase, resulting in the loss of the ability to resist compressive stress. Alterations in the expression of adhesion molecules, such as CD44 (Swissprot P22511), ICAM-1 (Swissprot P05362), and extracellular matrix protein, such as fibronectin and tenascin, follow. Eventually fibrous collagens are attacked by metalloproteases, and when the collagenous microskeleton is lost, repair by regeneration is impossible. There is significant immunological activity within the synovium during the course of inflammatory arthritis. While treatment during early stages is desirable, the adverse symptoms of the disease may be at least partially alleviated by treatment during later stages. Clinical indices for the severity of arthritis include pain, swelling, fatigue and morning stiffness, and may be quantitatively monitored by Pannus criteria. Disease progression in animal models may be followed by measurement of affected joint inflammation. Therapy for inflammatory arthritis may combine the subject treatment with conventional NSAID treatment. Generally, the subject treatment will not be combined with such disease modifying drugs as cyclosporin A, methotrexate, and the like.

A quantitative increase in myelin-autoreactive T cells with the capacity to secrete IFN-gamma is associated with the pathogenesis of MS and EAE, suggesting that autoimmune inducer/helper T lymphocytes in the peripheral blood of MS patients may initiate and/or regulate the demyelination process in patients with MS. The overt disease is associated with muscle weakness, loss of abdominal reflexes, visual defects and paresthesias. During the presymptomatic period there is infiltration of leukocytes into the cerebrospinal fluid, inflammation and demyelination. Family histories and the presence of the HLA haplotype DRB1*1501, DQA1*0102, DQB*0602 are indicative of a susceptibility to the disease. Markers that may be monitored for disease progression are the presence of antibodies in the cerebrospinal fluid, "evoked potentials" seen by electroencephalography in the visual cortex and brainstem, and the presence of spinal cord defects by MRI or computerized tomography. Treatment during the early stages of the disease will slow down or arrest the further loss of neural function.

Human IDDM is a cell-mediated autoimmune disorder leading to destruction of insulin-secreting β cells and overt hyperglycemia. T lymphocytes invade the islets of Langerhans, and specifically destroy insulin-producing β-cells. The depletion of β cells results in an inability to regulate levels of glucose in the blood. Overt diabetes occurs when the level of glucose in the blood rises above a specific level, usually about 250 mg/dl.

In humans a long presymptomatic period precedes the onset of diabetes. During this period there is a gradual loss of pancreatic β cell function. The disease progression may be monitored in individuals diagnosed by family history and genetic analysis as being susceptible. The most important genetic effect is seen with genes of the major histocompatibility locus (IDDM1), although other loci, including the insulin gene region (IDDM2) also show linkage to the disease (see Davies et al, supra and Kennedy et al. (1995) Nature Genetics 9:293–298). Markers that may be evaluated during the presymptomatic stage are the presence of insulitis in the pancreas, the level and frequency of islet cell antibodies, islet cell surface antibodies, aberrant expression of Class II MHC molecules on pancreatic β cells, glucose concentration in the blood, and the plasma concentration of insulin. An increase in the number of T lymphocytes in the pancreas, islet cell antibodies and blood glucose is indicative of the disease, as is a decrease in insulin concentration. After the onset of overt diabetes, patients with residual β cell function, evidenced by the plasma persistence of insulin C-peptide, may also benefit from the subject treatment, to prevent further loss of function.

The response of the host immune system to a graft, or of a graft towards the host (GVHD) is reduced by treatment with the subject suppressive vaccination. Grafts include the transplantation of cells, tissues and organs, such as the transfusion of blood or blood components, the grafting of bone, skin, bone marrow, etc., and the transplantation of tissues of the eye, pancreas, liver, kidney, heart, brain, bowel, lung, etc. Of interest are transplantation of hematopoietic cells, e.g. bone marrow, mobilized hematopoietic stem cells in peripheral blood, etc., transplantation of kidneys and transplantation of hearts. As used herein, a graft recipient is an individual to whom tissue or cells from another individual (donor), commonly of the same species, has been transferred, particularly where one or more of the Class I MHC antigens are different in the donor as compared to the recipient. However, in some instances xenogeneic, e.g. pig, baboon, etc., tissue, cells or organs will be involved. The graft recipient and donor are generally mammals, preferably human. For treatment of graft v. host disease, it may be desirable to vaccinate the graft donor prior to transplantation, so as to suppress the donor T cells.

Inflammatory diseases caused by bacterial and viral infection include viral meningitis and bacterial meningitis, herpes encephalitis and viral meningoencephalitis, viral hepatitis, e.g. Hepatitis A, B, C, D, etc. Diseases of interest also include inflammatory response to vaccination, particularly rabies vaccine, varicella zoster vaccine, measles vaccine, etc.

Mammalian species susceptible to inflammatory conditions include canines and felines; equines; bovines; ovines; etc. and primates, particularly humans. Animal models, particularly small mammals, e.g. murine, lagomorpha, etc. may be used for experimental investigations. Animal models of interest include those involved with the production of antibodies having isotypes associated with IL-4 production, e.g. IgE, IgG1 and IgG4. Other uses include investigations where it is desirable to investigate a specific effect in the absence of T cell mediated inflammation.

The following examples are offered by way of illustration and not by way of limitation.

EXPERIMENTAL

Example 1

Protection from Autoimmune Disease by DNA Vaccination

Materials and Methods

Figure 4:
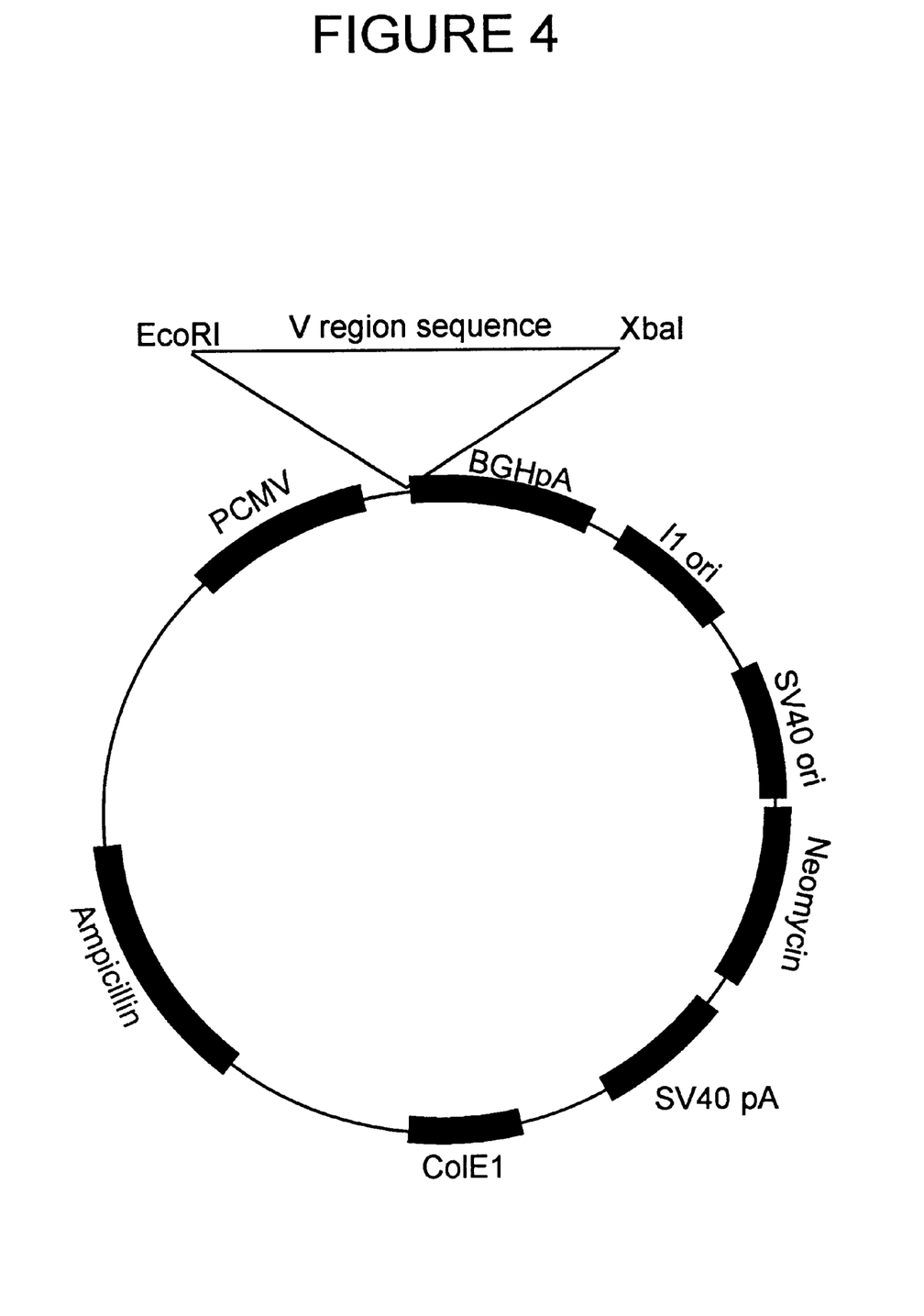
FIG. 4 shows an expression construct for suppressive vaccination.

Plasmid construction: RNA was isolated from normal PL/J mouse spleen cells, as described in Sambrook et al. Molecular cloning (Cold Spring Harbor, N.Y., 1989) and used as template for reverse transcriptase using poly(dT) (Boehringer Mannheim, Mannheim, Germany) as primer. This cDNA was then used for PCR using Taq polymerase (Stratagene, La Jolla, Calif.) with primers specific for Vβ5.1 5'-CCGGAATTCATGAATTCTGGGGTTGTCCAGTCT CCAAGA-3' [SEQ ID NO:1]
and 5'-TGCTCTAGATTAGCTGGCACAGAAGTACAC GGCAGA-3') [SEQ ID NO:2]
or Vβ8.2 (5'-CCGGAATTCATGGAGGCTGCAGTCACCCAAAG-3' [SEQ ID NO:3]
and 5'-TGCTCTAGATTAGCTGGCACAGMGTACACT GATGT-3') [SEQ ID NO:4].
These primers cover the complete V region (about 310 bp) and include EcoRI and XbaI sites used for cloning. The sequence of the Vβ5.1 amplification product is shown in SEQ ID NO:6, the Vβ8.2 amplification product is shown in SEQ ID NO:7. The PCR products were then cloned into pcDNA3 plasmid (Invitrogen, San Diego, Calif.), which was then used for mini-prep (Qiagen, Chatsworth, Calif.). DNA from colonies with an insert of the right length were amplified and sequenced, to verify the insertion of the right gene with an appropriate open reading frame. A map of the vector is shown in FIG. 4.

DNA injection and preparation: Large scale preparation of DNA was conducted using Maxi or Mega prep (Qiagen). Cardiotoxin (Sigman, St. Louis, Mo.) was prepared as described in Davis et al. (1993) FEBS Ltt. 333:146–150. The latter was found to enhance the efficiency of DNA vaccination. Fifty µl of cardiotoxin were injected into the tibialis anterior muscle of female, 6–8 week old PL/J mice (Jackson Laboratory, Bar-Harbor, Mass.). One week following injection, mice were injected with a total of 100 µg DNA in PBS (1 mg/ml), three times, with intervals of 6–7 days between each injection. To verify expression, muscle was removed from an injected mouse, and RNA was prepared. This RNA was used as a template for cDNA that was used for PCR, as described. PCR products of Vβ5.1 and Vβ8.2 were found only in the mice injected with the appropriate genes.

Disease Induction: pAc1-20 of rat myelin basic protein [SEQ ID NO:5] (Ac-ASQKRPSQRHGSKYLATAST) or gpMBP (Sakai et al., supra.) were mixed 1:1 with incomplete Freund's adjuvant (Difco, Detroit, Mich.) supplemented with killed Mycobacterium tuberculosis, strain H37 RA (Difco), to a final concentration of 1 mg/ml antigen and 2 mg/ml bacteria. The complete mRNA sequence encoding rat myelin basic protein has the Genbank accession number M25889. This mixture was then used for intradermal immunization of the treated PL/J mice, 50 µl in each footpad. Thereafter, mice were immunized with Bordetella pertussis toxin (200 ng, List Biological Laboratories, Campbell, Calif.), i.v., on the day of antigen inoculation and 48 hr. later. Adoptive transfer of EAE was accomplished by i.v. inoculation of $5\times10^6$ cells of T cell line per animal. All animals were followed for clinical signs of disease according to the following clinical scale: 0, no clinical disease; 1, tail weakness; 2, paraparesis, 3, paraplegia; 4, paraplegia with forelimb weakness or paralysis; 5, moribund or dead animals.

FACS staining: Cells were incubated ($5\times10^5$ cells/tube) with F23.2 (anti-Vβ8.2) or, as control, with KJ23 (anti-Vβ17a) antibodies, followed by goat anti-mouse conjugated to FITC (Jackson ImmunoResearch Laboratories, West Grove, Pa.) as described previously. The cells were also co-incubated with either anti-CD4 or anti-CD8 antibodies (Pharmingen) conjugated to PE. The cells were then analyzed for the presence of CD3+, CD4+ or CD8+ populations that express Vβ5 or Vβ8.2 TCR. Antibodies to the Vβ8.2 TCR in the sera of the vaccinated mice were analyzed as above. In addition, T cells were analyzed for their expression of CD3, CD4, CD8 and CD44 surface markers, using antibodies conjugated to FITC (Pharmingen).

Lymph node cells (LNC) Proliferation: LNC and spleen cells of immunized mice ($2\times10^5$/well) were cultured in the presence of different antigens. Cultures were set up in 200 µl RPMI 1640 medium supplemented with 2 mM glutamine, non-essential amino acids, 1 mM sodium pyruvate, 100 U/ml penicillin, 100 µg/ml streptomycin, 0.25 µg/ml fungizone (BioLab, Jerusalem, Israel), $5\times10^{-5}$ M β-mercaptoethanol (Fluka AG, Buchs, Switzerland) and 10 mM HEPES buffer (Sigma), referred to as enriched RPMI, containing 1% syngeneic normal mouse serum in round bottom 96-well microtiter plates (Nunc, Roskilde, Denmark). Following five days incubation, $^3$H-thymidine (0.5 µCi of 5 Ci/mmol, Nuclear research Center, Negev, Israel) was added. Sixteen hours later, cells were harvested and radioactivity counted.

Cytokines from Lymph Node Cells and T Cell Lines: LNC or spleen cells (1×107) were incubated in enriched RPMI with 1% syngeneic sera with 10 µg of the indicated peptides. Medium was collected 24 hrs later. The levels of IL-2 and γ-interferon were measured using the antibody pairs purchased from Pharmingen (La Jolla, Calif.), according to the manufacturer's instructions. The levels of IL-4, IL-10 and TNFα were measured using kits purchased from Genzyme (Cambridge, Mass.).

Anti-Ac1-20 antibodies: Mice were bled at the peak of disease, and antibodies against pAc1-20 were measured. Maxisorb microtiter plates were coated with 50 µl/well of 10 µg/ml Ac1-20 for 90 min. Thereafter, the plates were washed and blocked overnight with 10% FCS in PBS. Thereafter, the sera of the mice were incubated for 90 min. Plates were then washed and incubated for 75 minutes with goat anti-mouse IgG1 or IgG2a (Fc fragment specific) conjugated to alkaline phosphatase (Southern Biotechnology Associates, Birmingham Ala.). After washing, plates were incubated with the substrate, ABTS (Kirkegaard and Perry Laboratories, Gaithersburg, Md.) and read at 405 nm using an ELISA reader.

T cell Lines: Lymph node cells (LNC) (5–10×10⁶/ml) were incubated in enriched RPMI supplemented with 1% syngeneic sera and 10 μg/ml peptide Ac1-20 for 3 days. Thereafter, cells were washed and resuspended in rest medium (enriched RPMI, 10% FCS and 10% supernatant of spleen cells activated with conA) for 10 days. The cells were then activated in the presence of syngeneic irradiated spleen cells (10⁶/ml) and 10 μg/ml peptide Ac1-20 for 3 days, washed and incubated in resting medium for 3 days. Thereafter the cells were used for analysis.

T cell line proliferation assay: Proliferation assays were conducted as previously described above for LNC with minor changes: T cell lines (TCL) (10⁴) were incubated in round bottom plates (Corning, N.Y.) with 2×10⁵ irradiated syngeneic APC in a total volume of 250 μl of enriched RMPI and 10% FCS, and different concentrations of the peptide. After 24 hours, 100 μl were removed from each well for cytokine analysis. The remaining cells were incubated for an additional 24 hours, pulsed and harvested as in the LNC proliferation assay.

Statistical Analysis: Significance of differences were examined using Student's T test for proliferation and cytokine secretion assays. For disease severity the Mann-Whitney test was utilized. For analysis of GACS data Chi-square ($X^2$) was used. A value of $p<0.05$ was considered significant.

RESULTS

Figure 1A:
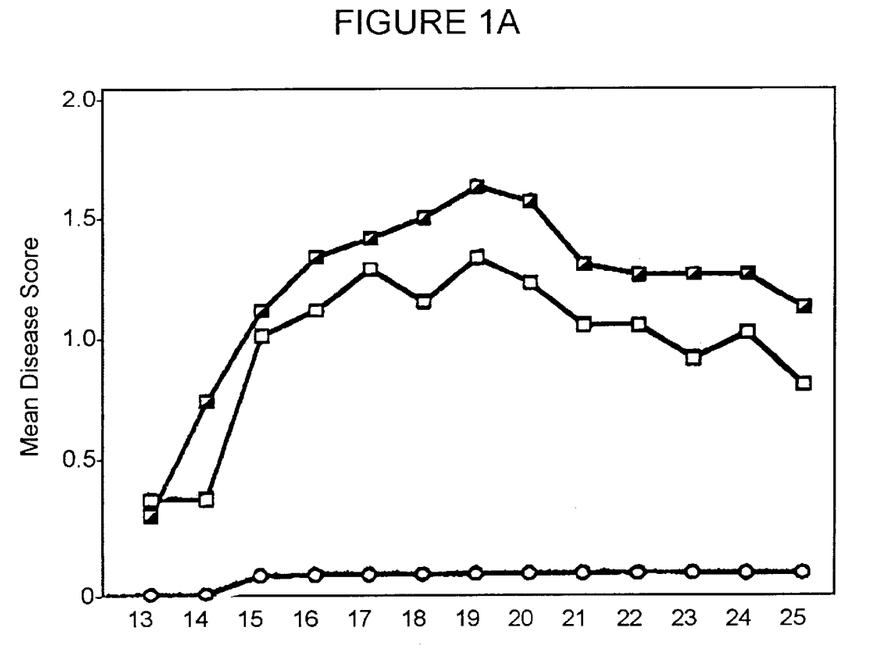
FIGS. 1A and 1B are graphs showing the effect of DNA vaccination of mice after active immunization with MBP Ac1-20 peptide (FIG. 1A) or intact MBP (FIG. 1B). Groups of 9–15 PL/J mice were injected s.c. in the foot pads with the peptide or protein. Mice were treated with DNA coding for V$\beta$5.1 (□), V$\beta$8.2 (○), or with PBS only (■). Shown is the mean disease score of all the mice in each group.

The Vβ8.2 gene of the T cell receptor was cloned in an expression vector and injected three times at weekly intervals into the tibialis anterior muscle of PL/J female mice, beginning one week following a single intramuscular injection of cardiotoxin. Control PL/J mice were immunized once with cardiotoxin and then at weekly intervals with the DNA coding for the Vβ5.1 variable region of the TCR. This TCR V region is not found on pathogenic T cell clones in H-2ᵘ mice. Following this immunization protocol, all mice were immunized with complete Freund's adjuvant containing either the myelin basic protein peptide Ac1-20, or guinea pig MBP. The mice vaccinated with the Vβ8.2 DNA were resistant to experimental autoimmune encephalitis (EAE) induced by the Ac1-20 peptide, while EAE was induced in the groups vaccinated with the control Vβ5.1 DNA, or with cardiotoxin alone. Only one mouse out of 14 vaccinated with the Vβ8.2 DNA developed mild paralysis of the hind limbs, while 11/15 and 10/13 mice were paralyzed or died in the respective control groups ($p<0.0001$), following immunization with pAc1-20. The data is shown in Table 1 and FIG. 1A.

TABLE 1

Active EAE Induction Following DNA Vaccination

| | EAE incidence | | | | | | | |
|---|---|---|---|---|---|---|---|---|
| DNA | Day 13 | Day 15 | Day 17 | Day 19 | Day 20 | Day 21 | Day 23 | Day 25 |
| (a) Disease induction with the peptide pAc1-20* | | | | | | | | |
| Vβ5.1 | 2/15 | 7/15 | 10/15 | 11/15 | 10/15 | 9/15 | 9/15 | 8/15 |
| Vβ8.2 | 0/14 | 1/14 | 1/14 | 1/14 | 1/14 | 1/14 | 1/14 | 1/14 |
| None | 2/13 | 4/13 | 7/113 | 9/13 | 10/13 | 7/13 | 7/13 | 7/13 |
| (b) Disease induction with gpMBP* | | | | | | | | |
| Vβ5.1 | 2/10 | 7/10 | 8/10 | 9/10 | 9/10 | 9/10 | 8/10 | 7/10 |
| Vβ8.2 | 0/9 | 2/9 | 5/9 | 5/9 | 5/9 | 5/9 | 4/9 | 3/9 |
| None | 2/10 | 5/10 | 8/10 | 9/10 | 9/10 | 9/10 | 8/10 | 8/10 |

*Disease was induced on day 0 as described in experimental procedures. Disease was monitored as described in experimental procedures. Shown are mice with clinical signs of EAE and the number of mice in each group.

Although perivascular infiltrates were present in the mice immunized with Vβ8.2, they were less extensive and less frequent than in mice immunized with Vβ5.1 when examined by an observer blinded to the treatment regimen. When scoring inflammatory infiltrates, significant differences were observed between mice treated with Vβ8.2 (scores 3.5±1.2 for brain meningeal infiltrates, 4.4±2.0 for brain parenchymal infiltrates) compared to mice treated with Vβ5.1 (28.2±4.0 for brain meningeal infiltrates, and 13.5±3 for brain parenchymal infiltrates) ($p<0.02$ for comparison of meningeal infiltrates, $p<0.03$ for comparison of parenchymal infiltrates) (histologic infiltrates were scored separately for brain parenchyma and meninges in a scale based in infiltrate size measured by number of cells per cuff).

Figure 1B:
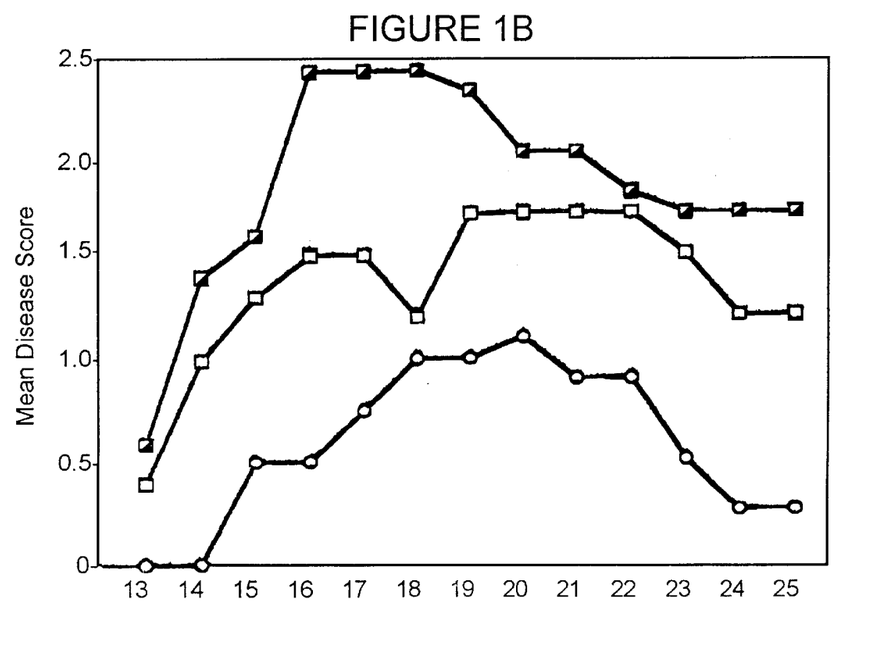

Although MBP Ac1-20 is the dominant epitope in the myelin basic protein molecule in PL/J mice, there are other pathogenic epitopes within this molecule, including MBP p35-47. T cell recognition of MBP p35-47 does not utilize the Vβ8.2 gene product. Therefore, it was determined whether DNA vaccination with the Vβ8.2 DNA is protective when EAE was induced with the whole myelin basic protein. In this case MBP Ac1-20 would be the dominant, but not exclusive pathogenic epitope, and other regions of MBP could be involved in pathogenesis. PL/J mice were vaccinated with Vβ8.2 DNA, and then induced disease with the whole myelin basic protein. PL/J mice vaccinated with Vβ8.2 DNA developed EAE when they were immunized with guinea pig MBP, although disease occurred at a lower frequency ($p<0.04$, from day 15 onward) compared with the mice vaccinated with the control DNA, or cardiotoxin alone, shown in FIG. 1B and Table 1.

Mice were analyzed for titers of antibodies directed to Vβ8.2 TCR. Mice vaccinated with the DNA construct containing the Vβ8.2 DNA produced antibodies to the Vβ8.2 expressed on T cells. Sera from mice vaccinated with the Vβ8.2 DNA stained 76.9±12.1% cells of a Vβ8.2⁺ T cell line, reactive with MBP Ac1-20, while only 4.3±3% of the cells were stained with the sera from the control mice, a figure that is similar to the background staining with normal mouse sera (3.8±2.7, $p<0.01$). To test whether those anti-Vβ8.2 antibodies depleted the Vβ8.2 positive T cells, lymph node cells (LNC) and spleen cells from the protected mice and controls were stained for the presence of this cell population. Mice vaccinated with the Vβ8.2 DNA have similar levels of Vβ8.2 positive T cells, as compared to the control groups, as well as when compared to normal mice.

It was then determined whether the DNA vaccination altered the response of the Vβ8.2 T cells, rendering them unable to mount a pathogenic response. Lymph nodes were taken from the protected animals and from the controls, in order to test whether anergy of the Vβ8.2 positive T cells to the immunizing peptide could account for the protection. It was found that lymph nodes taken from the PL/J mice were able to respond by proliferation to the immunizing peptide, with a smaller stimulation index than the cells taken from the control mice, either treated by injection with Vβ5.1 or with cardiotoxin alone. Thus, DNA vaccination did not induce anergy.

Figure 2A:
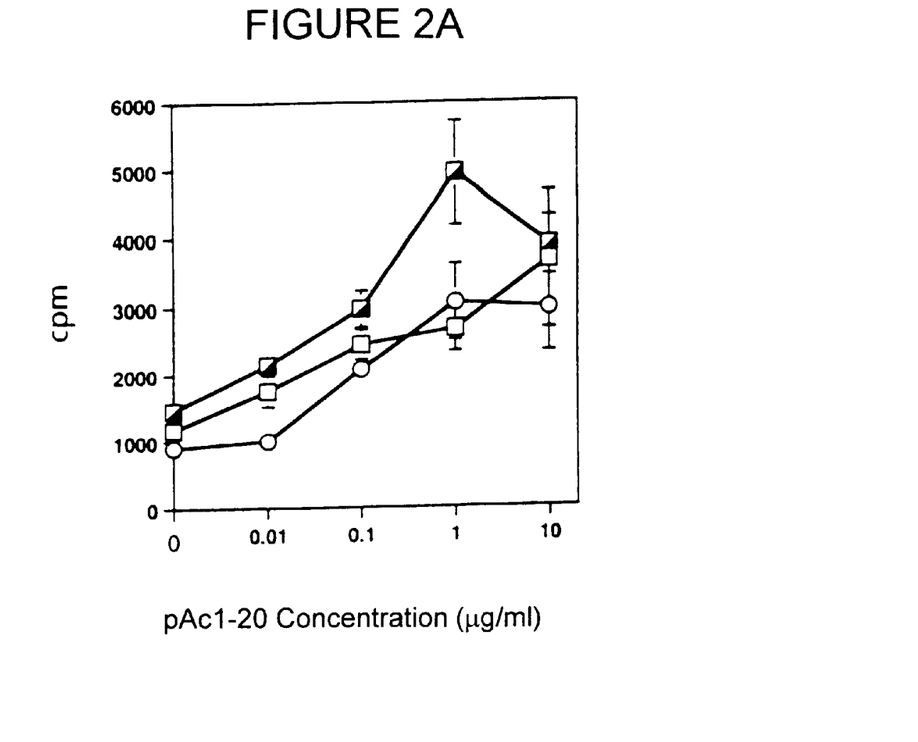
Figure 2B:
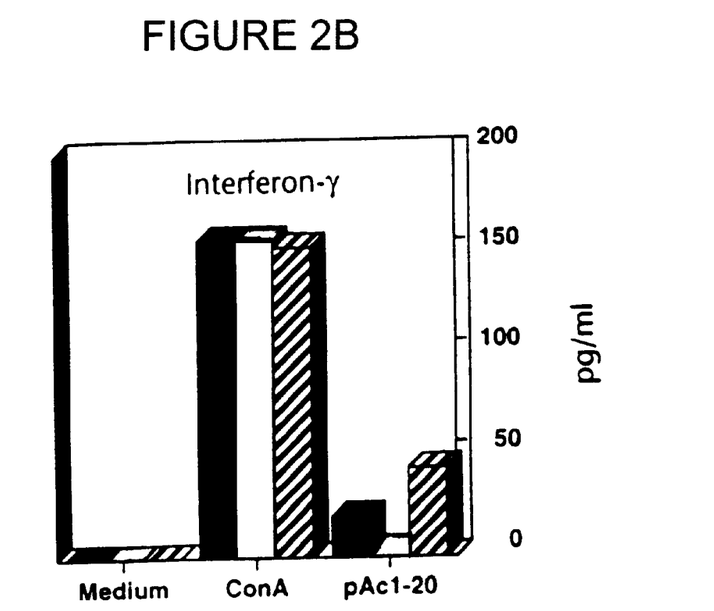
Figure 2C:
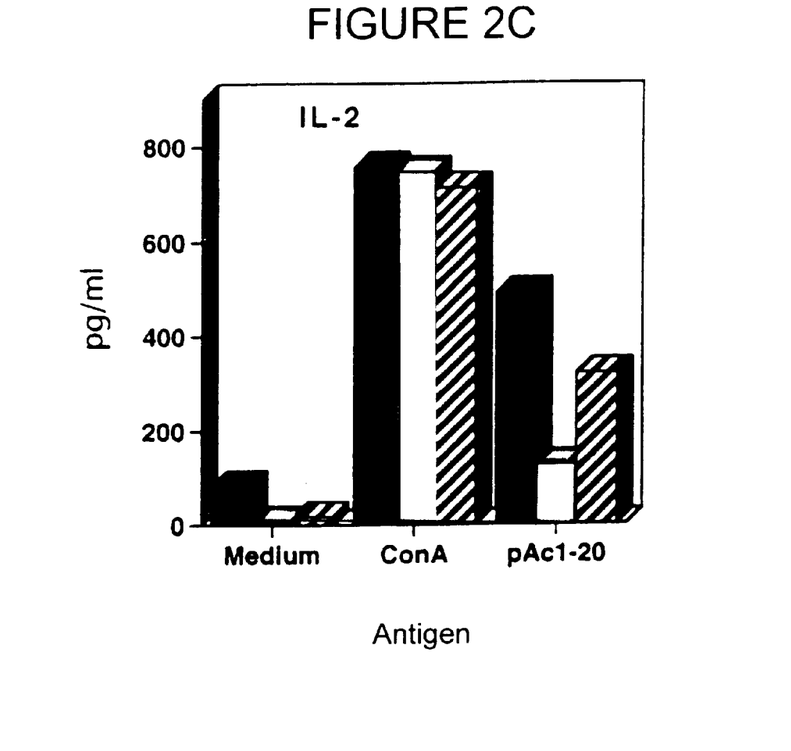
Figure 2D:
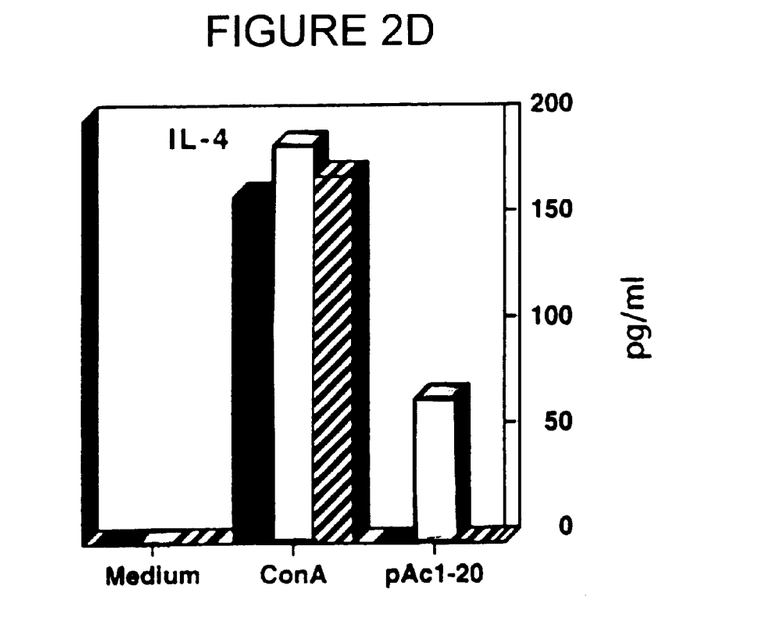
Figure 3A:
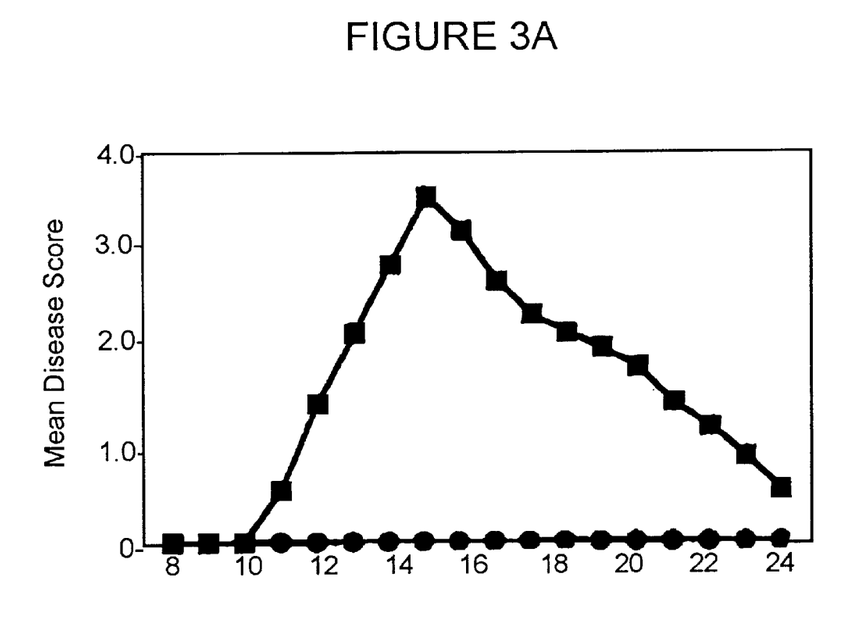
Figure 3B:
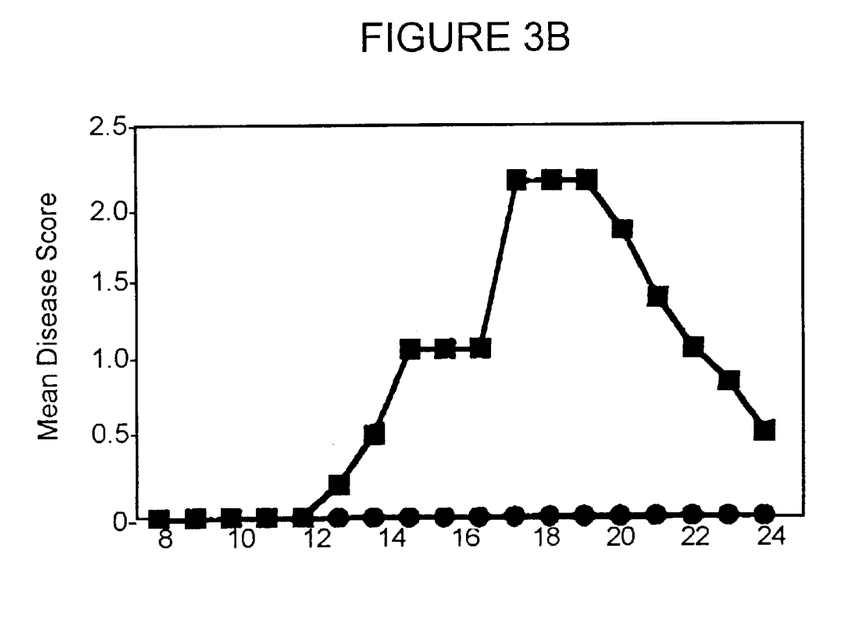

It was found that LNC from mice vaccinated with Vβ8.2 DNA produced much lower levels of γ-interferon (p<0.002) and IL-2 (p<0.0015) after activation with MBP Ac1-20, when compared to controls (shown in FIGS. 2A and 2B). IL-2 and γ-interferon are cytokines produced by T cells of the Th1 phenotype. In contrast, the LNC taken from the mice vaccinated with Vβ8.2 DNA produced elevated levels of the Th2 cytokine, IL-4, following stimulation with MBP Ac1-20 (p<0.04), shown in FIG. 2C. These data indicate that the phenotype of the immune response in Vβ8.2 vaccinated mice, immunized with an antigen recognized by T cells expressing Vβ8.2 TCR, had undergone a cytokine shift from Th1 to Th2.

IL-4 induces a class switch of antibody from IgG2a to IgG1 isotype. This switch is a hallmark of Th1 to Th2 shift in vivo. The isotype of antibodies directed to the immunizing peptide, MBP Ac1-20, was analyzed with and without DNA vaccination to Vβ8.2. Mice vaccinated with Vβ8.2 DNA produced higher levels of anti-Ac1-20 antibodies of the IgG1 isotype, and lower levels of antibody of the IgG2a isotype, in comparison to the control mice (p<0.01). These data confirm the idea that DNA vaccination to Vβ8.2 results in a cytokine shift in the response of T cells to MBP Ac1-20, an antigen predominantly recognized by T cells bearing Vβ8.2. This could account for the protection against the development of EAE, since EAE is known to be a Th1 type disease. Moreover, injection of IL-4 protects mice from development of EAE.

To analyze the role of T cells in the protection mechanism, short term T cell lines were raised Vβ8.2 vaccinated and control mice. Four T cell lines derived from spleen and lymph node were tested extensively for proliferation and cytokine responses, two from mice vaccinated with Vβ8.2 DNA (TCL 8.2-Sp and 8.2-LN) and two from controls (TCL PL-LN and PL-Sp). All T cell lines were 85–90% Vβ8.2$^+$, 95% CD44$^+$, and CD3$^+$, CD4$^+$, CD8$^-$. All T cell lines proliferated in the presence of the peptide Ac1-20 (p<0.003 to p<0.0001 in comparison to background). In contrast to its relatively low proliferative response, the line PL-Sp produced high levels of γ-interferon on stimulation with peptide MBP Ac1-20, similar to the levels produced by the line PL-LN, and higher than the levels produced by the two lines isolated from mice vaccinated with Vβ8.2 DNA (p<0.015).

The T cells isolated from the mice vaccinated with Vβ8.2 DNA produced IL-4, while no secretion of that cytokine was observed from the TCL isolated from the control mice. The two T cell lines isolated from control mice with EAE produced significantly higher levels of TNFα in comparison to the lines isolated from protected mice (p<0.02). The latter is in agreement with the findings that encephalitogenic T cell lines produce high levels of TNFα. These findings all serve to indicate that DNA vaccination to the TCR Vβ8.2 induced a shift in the phenotype of T cells responding to the antigen MBP Ac1-20, and indicated a shift from Th1 to Th2.

To determine whether T cell lines reactive to MBP Ac1-20 from vaccinated animals could induce EAE, TCL were raised from mice immunized with MBP Ac1-20 from mice immunized with either Vβ8.2 or mice given Vβ5.1. Five million cells were injected intravenously and the clinical course of disease was monitored. It was found that T cell lines reactive to MBP Ac1-20 from Vβ8.2 immunized mice failed to induce EAE, whereas control mice developed classic EAE beginning on day 12.

It was further determined whether the Th2 T cell lines directed to MBP Ac1-20 derived from mice immunized with Vβ8.2 DNA would suppress EAE. It was found that mice receiving five million TH2 cells did not get EAE following immunization on the same day with MBP Ac1-20 in CFA, whereas mice receiving MBP Ac1-20 in CFA developed grade 2 EAE. Thus, these Th2 T cells were able to suppress EAE.

The results described herein demonstrate that DNA vaccination with a T-cell receptor V gene commonly found on pathogenic T cells is able to prevent autoimmune disease. When vaccinated with a variable region that recognizes an immunodominant peptide, induction of disease by the complete protein is also reduced. The DNA vaccination induces a shift in the cytokine production of T-cells that utilize the relevant V gene segment from Th1 to Th2, accompanied by a shift in the antibody isotype produced against the cognate antigen. These Th2 cytokines counteract the effects of inflammatory cytokines.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of suppressing Th1 type T cell response in a myelin basic protein associated autoimmune disease, the method comprising:

injecting into muscle tissue of a mammalian host a DNA expression vector comprising: a sequence encoding the variable region of a T cell receptor that (a) is selected from the group consisting of mouse Vβ8.2, mouse Vβ17a, human Vβ5, human Vβ6, human Vβ4 subfamily and human Vβ12 subfamily, (b) recognizes an epitope of myelin basic protein, and (c) is under the regulatory control of a promoter that is active in said muscle tissue, wherein said expression cassette is incorporated into muscle cells of said host and said sequence is expressed at levels sufficient to suppress said Th1 type T cell response, and wherein said suppression of the TH1 type T cell response prevents onset of said myelin basic protein associated autoimmune disease.

2. A method according to claim 1, further comprising the step of injecting cardiotoxin into said muscle tissue, prior to said introducing step.

3. A method according to claim 1, wherein said DNA expression vector is a plasmid.

4. A method according to claim 3, wherein said plasmid is transiently expressed in said muscle cells.

5. A method according to claim 1, wherein said mammalian host is a mouse and wherein said sequence encoding the variable region of a T cell receptor is mouse Vβ8.2.

6. A method according to claim 1, wherein said autoimmune disease is multiple sclerosis.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 39 base pairs
      (B) TYPE: nucleic acid
      (C) STRANDEDNESS: single
      (D) TOPOLOGY: linear

```
    (ii) MOLECULE TYPE: other nucleic acid
         (A) DESCRIPTION: /desc = "Primers"

(xi) SEQUENCE DESCRIPTION: SEQ ID NO:1:

CCGGAATTCA TGAATTCTGG GGTTGTCCAG TCTCCAAGA                                   39

(2) INFORMATION FOR SEQ ID NO:2:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primers"

(xi) SEQUENCE DESCRIPTION: SEQ ID NO:2:

TGCTCTAGAT TAGCTGGCAC AGAAGTACAC GGCAGA                                      36

(2) INFORMATION FOR SEQ ID NO:3:

(i) SEQUENCE CHARACTERISTICS:
         (A) LENGTH: 32 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primers"

(xi) SEQUENCE DESCRIPTION: SEQ ID NO:3:

CCGGAATTCA TGGAGGCTGC AGTCACCCAA AG                                          32

(2) INFORMATION FOR SEQ ID NO:4:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primers"

(xi) SEQUENCE DESCRIPTION: SEQ ID NO:4:

TGCTCTAGAT TAGCTGGCAC AGAAGTACAC TGATGT                                      36

(2) INFORMATION FOR SEQ ID NO:5:

(i) SEQUENCE CHARACTERISTICS:
         (A) LENGTH: 20 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:5:

Ala Ser Gln Lys Arg Pro Ser Gln Arg His Gly Ser Lys Tyr Leu Ala
1               5                   10                  15

Thr Ala Ser Thr
            20

(2) INFORMATION FOR SEQ ID NO:6:

(i) SEQUENCE CHARACTERISTICS:
         (A) LENGTH: 299 base pairs
         (B) TYPE: nucleic acid
```

-continued

```
            (C) STRANDEDNESS: double
            (D) TOPOLOGY: linear (ii) MOLECULE TYPE: other nucleic acid
            (A) DESCRIPTION: /desc = "Primers"

(xi) SEQUENCE DESCRIPTION: SEQ ID NO:6:

CCGGAATTCA TGAATTCTGG GGTTGTCCAG TCTCCAAGAT ACATAATCAA AGGAAAGGGA      60

GAAAGGTCCA TTCTAAAATG TATTCCCATC TCTGGACATC TCTCTGTGGC CTGGTATCAA     120

CAGACTCAGG GGCAGGAACT AAAGTTCTTC ATTCAGCATT ATGATAAAAT GGAGAGAGAT     180

AAAGGAAACC TGCCCAGCAG ATTCTCAGTC CAACAGTTTG ATGACTATCA CTCTGAGATG     240

AACATGAGTG CCTTGGAGCT AGAGGACTCT GCCGTGTACT TCTGTGCTAA TCTAGAGCA      299

(2) INFORMATION FOR SEQ ID NO:7:

(i) SEQUENCE CHARACTERISTICS:
            (A) LENGTH: 303 base pairs
            (B) TYPE: nucleic acid
            (C) STRANDEDNESS: double
            (D) TOPOLOGY: linear (ii) MOLECULE TYPE: other nucleic acid
            (A) DESCRIPTION: /desc = "Primers"

(xi) SEQUENCE DESCRIPTION: SEQ ID NO:7:

CCGGAATTCA TGGAGGCTGC AGTCACCCAA AGCCCAAGAA ACAAGGTGGC AGTAACAGGA      60

GGAAAGGTGA CATTGAGCTG TAATCAGACT AATAACCACA ACAACATGTA CTGGTATCGG     120

CAGGACACGG GGCATGGGCT GAGGCTGATC CATTATTCAT ATGGTGCTGG CAGCACTGAG     180

AAAGGAGATA TCCCTGATGG ATACAAGGCC TCCAGACCAA GCCAAGAGAA CTTCTCCCTC     240

ATTCTGGAGT TGGCTACCCC CTCTCAGACA TCAGTGTACT TCTGTGCCAG CTAATCTAGA     300

GCA                                                                   303
```